(12) United States Patent
Kawayoke (10) Patent No.: US 10,485,412 B2
(45) Date of Patent: Nov. 26, 2019

(54) IMAGE PICKUP APPARATUS AND ENDOSCOPE

(71) Applicant: OLYMPUS CORPORATION, Tokyo (JP)

(72) Inventor: Shoichiro Kawayoke, Nagano (JP)

(73) Assignee: OLYMPUS CORPORATION, Tokyo (JP)

( * ) Notice: Subject to any disclaimer, the term of this patent is extended or adjusted under 35 U.S.C. 154(b) by 624 days.

(21) Appl. No.: 15/172,203

(22) Filed: Jun. 3, 2016

(65) Prior Publication Data

US 2016/0278620 A1    Sep. 29, 2016

Related U.S. Application Data

(63) Continuation of application No. PCT/JP2014/074547, filed on Sep. 17, 2014.

(30) Foreign Application Priority Data

Dec. 4, 2013   (JP) .................. 2013-251239

(51) Int. Cl.
*A61B 1/05* (2006.01)
*A61B 1/00* (2006.01)
(Continued)

(52) U.S. Cl.
CPC .............. *A61B 1/051* (2013.01); *A61B 1/005* (2013.01); *A61B 1/0011* (2013.01);
(Continued)

(58) Field of Classification Search
USPC ........................................................ 600/109
See application file for complete search history.

(56) References Cited

U.S. PATENT DOCUMENTS 8,698,887 B2 *   4/2014   Makino ................ H04N 5/2254
                                                                       348/76
9,572,482 B2 *   2/2017   Lin ....................... A61B 1/0011
(Continued)

FOREIGN PATENT DOCUMENTS

JP    2002-291693 A    10/2002
JP    2003-305004 A    10/2003
(Continued)

OTHER PUBLICATIONS

International Search Report dated Jan. 13, 2015 issued in PCT/JP2014/074547.

*Primary Examiner* — Timothy J Neal
*Assistant Examiner* — Jae Woo
(74) *Attorney, Agent, or Firm* — Scully, Scott, Murphy & Presser, P.C.

(57) ABSTRACT

An image pickup apparatus includes an image pickup device on which a light receiving section is formed, a heat transfer member made of a material having thermal conductivity equal to or higher than 15 W/(m·K), the heat transfer member including a wiring board, a joining section joined to the image pickup device, a bending section extended from the joining section, and a fixed section extended from the bending section, and a housing made of metal, an inner surface of which is in contact with a part of the fixed section of the heat transfer member housed on an inside.

15 Claims, 7 Drawing Sheets

(51) Int. Cl.
  *A61B 1/005* (2006.01)
  *H04N 5/232* (2006.01)
  *A61B 1/12* (2006.01)
  *G02B 23/24* (2006.01)
  *H04N 5/225* (2006.01)

(52) U.S. Cl.
  CPC ...... *A61B 1/00124* (2013.01); *A61B 1/00163* (2013.01); *A61B 1/128* (2013.01); *G02B 23/2492* (2013.01); *H04N 5/2253* (2013.01); *H04N 5/232* (2013.01); *H04N 2005/2255* (2013.01)

(56) References Cited

U.S. PATENT DOCUMENTS

| | | | | |
|---|---|---|---|---|
| 9,622,649 B2* | 4/2017 | Lin | | A61B 1/0011 |
| 2003/0095781 A1* | 5/2003 | Williams | | A61B 17/02 |
| | | | | 385/146 |
| 2005/0171408 A1* | 8/2005 | Parker | | A61B 90/35 |
| | | | | 600/249 |
| 2007/0185379 A1* | 8/2007 | Newman | | A61B 1/00052 |
| | | | | 600/110 |
| 2009/0315986 A1* | 12/2009 | Ohara | | A61B 1/05 |
| | | | | 348/65 |
| 2009/0322867 A1* | 12/2009 | Carrey | | A61B 1/00039 |
| | | | | 348/77 |
| 2010/0185052 A1* | 7/2010 | Chang | | A61B 1/0011 |
| | | | | 600/112 |
| 2010/0314986 A1* | 12/2010 | Gershaw | | F21K 9/69 |
| | | | | 313/46 |
| 2011/0092769 A1* | 4/2011 | Kokubo | | A61B 1/05 |
| | | | | 600/109 |
| 2011/0118549 A1* | 5/2011 | Han | | A61B 1/04 |
| | | | | 600/109 |
| 2011/0211053 A1* | 9/2011 | Nakayama | | A61B 1/051 |
| | | | | 348/76 |
| 2012/0075446 A1 | 3/2012 | Nakamura | | |
| 2012/0197081 A1* | 8/2012 | Kimura | | A61B 1/00124 |
| | | | | 600/110 |
| 2013/0131451 A1* | 5/2013 | Dillinger | | A61B 1/0676 |
| | | | | 600/127 |
| 2013/0271588 A1* | 10/2013 | Kirma | | A61B 1/00091 |
| | | | | 348/76 |
| 2013/0274551 A1* | 10/2013 | Kirma | | A61B 1/00091 |
| | | | | 600/104 |
| 2013/0310644 A1* | 11/2013 | Ichimura | | A61B 1/127 |
| | | | | 600/109 |
| 2014/0213850 A1* | 7/2014 | Levy | | A61B 1/00137 |
| | | | | 600/156 |
| 2014/0296643 A1* | 10/2014 | Levy | | A61B 1/00096 |
| | | | | 600/160 |
| 2014/0296866 A1* | 10/2014 | Salman | | A61B 1/018 |
| | | | | 606/109 |
| 2015/0297069 A1* | 10/2015 | Coppersmith | | F21V 29/70 |
| | | | | 600/132 |
| 2015/0335233 A1* | 11/2015 | Pilz | | A61B 1/00128 |
| | | | | 600/476 |
| 2016/0008088 A1* | 1/2016 | Vayser | | A61B 90/57 |
| | | | | 600/178 |
| 2017/0071462 A1* | 3/2017 | Wieters | | A61B 1/043 |
| 2017/0242240 A1* | 8/2017 | Krivopisk | | H04N 5/374 |
| 2018/0035878 A1* | 2/2018 | Nara | | A61B 1/0011 |

FOREIGN PATENT DOCUMENTS

| | | |
|---|---|---|
| JP | 2011-200338 A | 10/2011 |
| JP | 2011-200401 A | 10/2011 |
| JP | 2012-050756 A | 3/2012 |
| JP | 2012-071064 A | 4/2012 |
| JP | 2013-233215 A | 11/2013 |

* cited by examiner

IMAGE PICKUP APPARATUS AND ENDOSCOPE

CROSS REFERENCE TO RELATED APPLICATION

This application is a continuation application of PCT/JP2014/074547 filed on Sep. 17, 2014 and claims benefit of Japanese Application No. 2013-251239 filed in Japan on Dec. 4, 2013, the entire contents of which are incorporated herein by this reference.

BACKGROUND OF THE INVENTION

1. Field of the Invention

The present invention relates to an image pickup apparatus in which an image pickup device and a heat transfer member joined to the image pickup device are housed in a housing and an endoscope including the image pickup apparatus.

2. Description of the Related Art

An image pickup device including a semiconductor, on a principal plane of which a light receiving section is formed, is small in size. Therefore, the image pickup device is used in an electronic endoscope and the like. However, when temperature of the image pickup device rises during operation, in some case, the image pickup device is deteriorated or image quality is deteriorated by thermal noise.

Therefore, an image pickup apparatus that suppresses a temperature rise of an image pickup device by transferring, with a member having high thermal conductivity, heat generated by the image pickup device is reported.

For example, Japanese Patent Application Laid-Open Publication No. 2011-200338 discloses an electronic endoscope including an image pickup apparatus in which one end portion of a flexible substrate is connected to a CCD (an image pickup device) and the other end of the flexible substrate is closely attached to an inner wall surface of a protection frame made of metal having high thermal conductivity. The protection frame includes a spring section and surely comes into contact with an inner circumferential surface of a cylindrical section. Consequently, heat generated from the CCD is radiated to the protection frame.

SUMMARY OF THE INVENTION

An image pickup apparatus in an embodiment of the present invention includes: an image pickup device including a first principal plane and a second principal plane, in which a light receiving section is formed on the first principal plane; a wiring board including a device electrode pad connected to an external connection terminal of the image pickup device and a wire, one end of which is connected to the device electrode pad; a heat transfer member, which is made of a material having thermal conductivity equal to or higher than 15 W/(m·K), including a joining section joined to the second principal plane of the image pickup device, a bending section extended from the joining section, and a fixed section extended from the bending section; and a housing made of metal, an inner surface of which is in contact with a part of the fixed section of the heat transfer member housed on an inside.

An endoscope in another embodiment of the present invention includes an image pickup apparatus including: an image pickup device including a first principal plane and a second principal plane, in which a light receiving section is formed on the first principal plane; a wiring board including a device electrode pad connected to an external connection terminal of the image pickup device and a wire, one end of which is connected to the device electrode pad; a heat transfer member, which is made of a material having thermal conductivity equal to or higher than 15 W/(m·K), including a joining section joined to the second principal plane of the image pickup device, a bending section extended from the joining section, and a fixed section extended from the bending section; and a housing made of metal, an inner surface of which is in contact with a part of the fixed section of the heat transfer member housed on an inside.

DETAILED DESCRIPTION OF THE PREFERRED EMBODIMENTS

First Embodiment

An image pickup apparatus 1 in the present embodiment is small in diameter and very small in size because the image pickup apparatus 1 is disposed, for example, at a distal end portion of an electronic endoscope.

Figure 1:
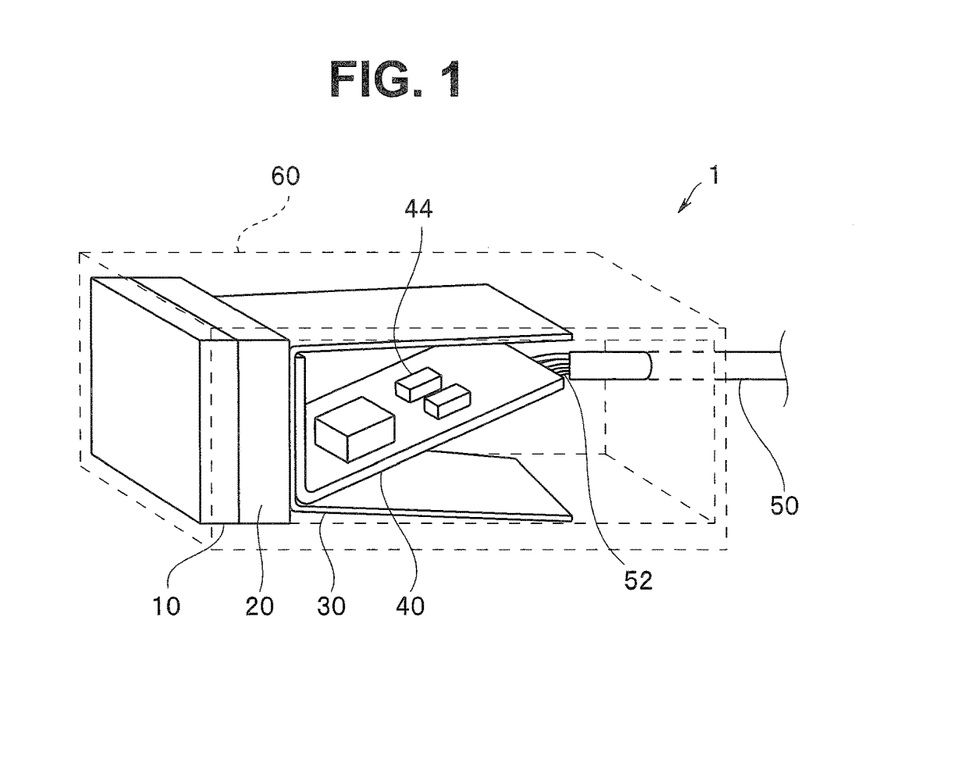
FIG. 1 is a perspective view of an image pickup apparatus in a first embodiment.
Figure 2:
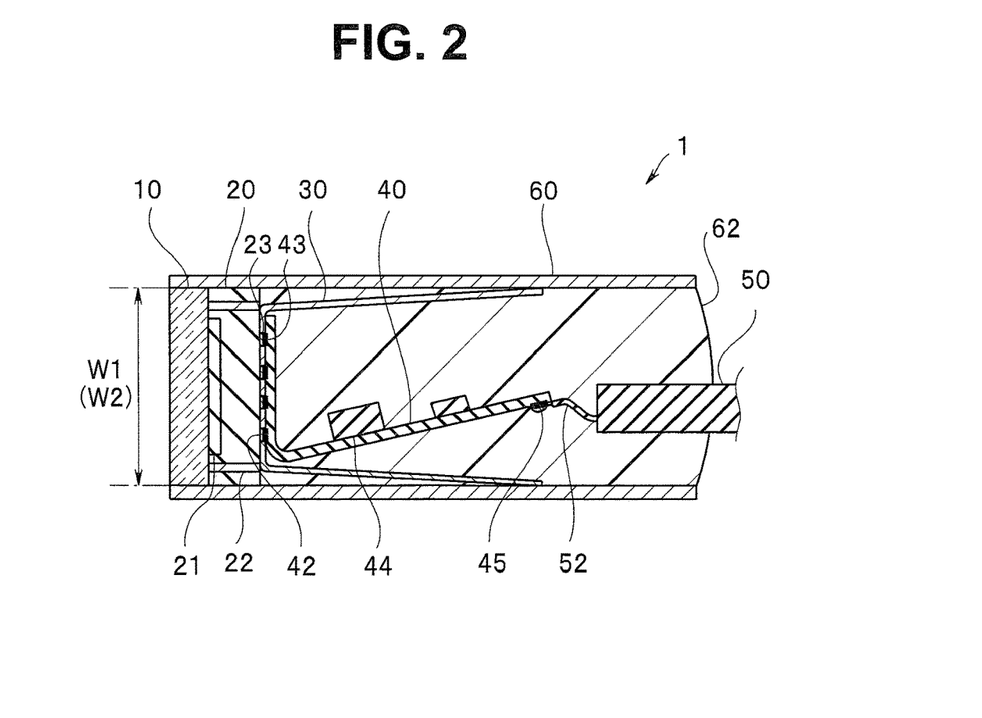
FIG. 2 is a sectional view of the image pickup apparatus in the first embodiment.
Figure 3:
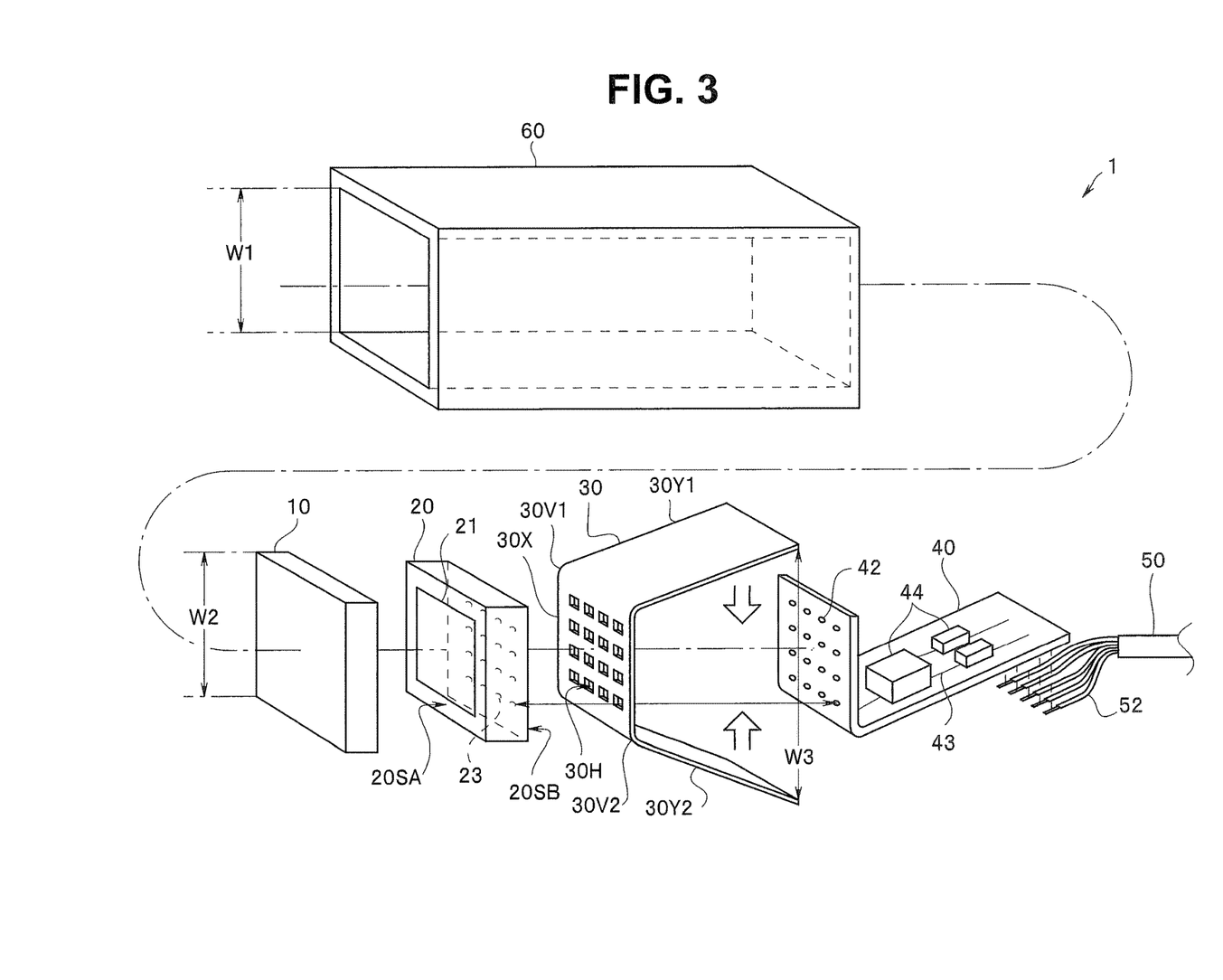
FIG. 3 is an exploded view of the image pickup apparatus in the first embodiment.

As shown in FIG. 1, FIG. 2, and FIG. 3, the image pickup apparatus 1 includes a cover glass 10, an image pickup device 20, a heat transfer member 30, a wiring board 40, a cable 50, and a housing 60. An image pickup unit including the cover glass 10, the image pickup device 20, the heat transfer member 30, and the wiring board 40 is housed on an inside of the housing 60. Note that, as shown in FIG. 2 and the like, resin 62 is filled in the inside of the housing 60. However, the resin 62 is not shown in FIG. 1 and the like.

The image pickup device 20 exchanges electric signals with a processor (not shown in the figure) connected to the cable 50 via the wiring board 40. That is, a plurality of external connection terminals 23 of the image pickup device 20 are joined to respective device electrode pads 42 (hereinafter referred to as "electrode pads 42") at one end of a wire 43 of the wiring board 40. A plurality of cable electrode pads 45 (hereinafter referred to as "electrode pads 45") at the other end of the wire 43 are respectively connected to lead wires 52 of the signal cable 50.

The image pickup apparatus 1 includes the heat transfer member 30. A part of the heat transfer member 30 is joined to the image pickup device 20 and transfers heat generated by the image pickup device 20 to the housing 60 with which another part of the heat transfer member 30 is in contact.

The components of the image pickup apparatus 1 are explained below.

The image pickup device 20 is a substantially rectangular parallelepiped chip in which a light receiving section 21 including a solid-state image pickup circuit is formed on a first principal plane 20SA. Note that the solid-state image pickup circuit includes a CCD or a CMOS sensor. The image pickup device 20 may be a back illuminated type.

The external connection terminal 23 for exchanging signals with the light receiving section 21 is formed on a second principal plane 20SB via a through-wire 22. That is, the plurality of external connection terminals 23 are disposed on the second principal plane 20SB in an array shape. Note that a wire from the light receiving section 21 to the through-wire 22 is present on the first principal plane 20SA and a wire from the through-wire 22 to the external connection terminal 23 is present on the second principal plane 20SB. However, the wires are not shown in the figure.

The cover glass 10 is bonded to the first principal plane 20SA of the image pickup device 20 via an adhesive layer (not shown in the figure). As explained below, in the image pickup apparatus 1, after a transparent wafer is bonded to a semiconductor wafer on which a plurality of light receiving sections and the like are fondled, the bonded wafers are singulated by dicing. Therefore, a plan view dimension of the image pickup device 20 and a plan view dimension of the cover glass 10 are the same. Note that, although the cover glass 10 has a protection function for the light receiving section 21, the cover glass 10 is not an essential component of the image pickup apparatus 1.

The wiring board 40 is a flexible wiring board including flexible resin such as polyimide as a base material and including the wire 43 made of copper or the like. The wiring board 40 may be a single-layer wiring board or may be a multi-layer wiring board in which wiring layers are formed at least on both surfaces. The electrode pad 42 is formed on a distal end side of the wiring board 40. The electrode pad 45 (see FIG. 2) is formed on a rear end side. The electrode pad 42 and the electrode pad 45 are electrically connected by the wire 43. A connection pad (not shown in the figure) is formed in the wire 43 of the wiring board 40. An electronic component 44 such as a chip capacitor is mounted on the connection pad. That is, the wire 43 configures an electronic circuit that processes a signal inputted from the image pickup device 20 and outputs the signal to the signal cable 50.

Note that, as shown in FIG. 1 to FIG. 3 and the like, the wiring board 40 is bent halfway and fit within a projection surface of a principal plane of the image pickup device 20.

The heat transfer member 30 includes a joining section 30X joined to the second principal plane 20SB of the image pickup device 20, bending sections 30V1 and 30V2 extended from the joining section 30X, and fixed sections 30Y1 and 30Y2 extended from the respective bending sections 30V1 and 30V2. Note that, in the following explanation, when a plurality of components having the same function are referred to, a last one numerical character of a sign of the components is sometimes omitted. For example, each of the bending sections 30V1 and 30V2 is referred to as bending sections 30V.

When the heat transfer member 30 is housed on the inside of the housing 60, the fixed section 30Y is pressed against an inner surface of the housing 60 by an urging force and surely comes into contact with the inner surface of the housing 60 made of metal. That is, the bending section 30V, which is a spring, presses the fixed section 30Y against the inner surface of the housing 60.

Since heat generated by the image pickup device 20 is transferred to the housing 60 via the heat transfer member 30 having high thermal conductivity, the heat is efficiently radiated. Therefore, temperature of the image pickup device 20 does not excessively rise during operation. Therefore, the image pickup device 20 is not deteriorated. Image quality is not deteriorated by thermal noise.

Note that, in the image pickup apparatus 1, the external connection terminal 23 is present on the second principal plane 20SB of the image pickup device 20. Therefore, a through-hole 30H is present in a position opposed to the external connection terminal 23 of the heat transfer member 30, in other words, in a position opposed to the electrode pad 42 of the wiring board 40.

Figure 4:
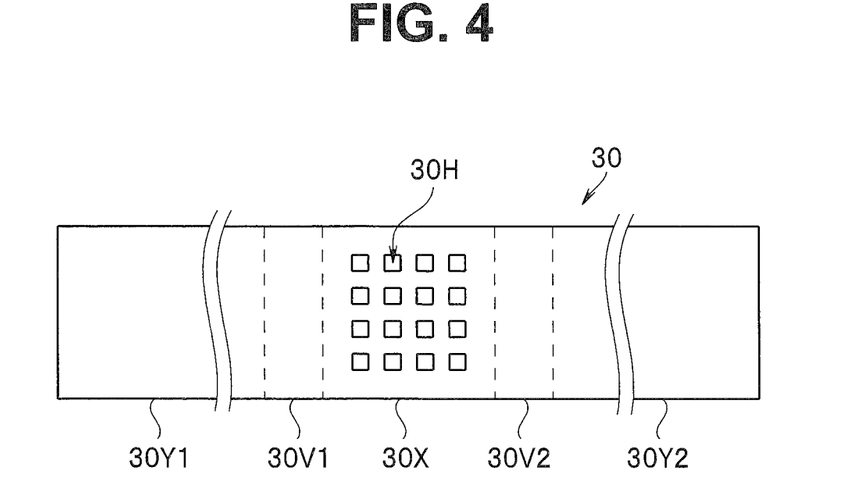
FIG. 4 is a plan view of a heat transfer member of the image pickup apparatus in the first embodiment.

As shown in FIG. 4, a plan view shape of the joining section 30X of the heat transfer member 30 is substantially rectangular like the image pickup device 20. The bending section 30V and the fixed section 30Y extend from two opposed sides among four sides of the joining section 30X. That is, the heat transfer member 30 includes an extended plurality of bending sections 30V and an extended plurality of fixed sections 30Y. However, the bending sections 30V and the fixed sections 30Y are integral. A boundary between the bending sections 30V and the fixed sections 30Y cannot be clearly distinguished.

The heat transfer member 30 is a thin plate made of a metal material having high thermal conductivity and elasticity such as stainless steel, copper, phosphor bronze, or a copper alloy. As shown in FIG. 3, the bending section 30V is bent and plastically deformed before being housed in the inside of the housing 60.

In FIG. 3, length between an end portion of the fixed section 30Y1 and an end portion of the fixed section 30Y2 of the heat transfer member 30, in which the bending section 30V is plastically deformed, is shown as W3. The length W3 is larger than an inner dimension W1 of the housing 60.

Therefore, when being housed in the inside of the housing 60, the fixed section 30Y is pressed against the inner surface of the housing 60 by an urging force and surely comes into contact with the housing 60.

A material of the heat transfer member 30 has thermal conductivity $\lambda$ of 15 W/(m·K) or more. That is, as the heat transfer member 30, for example, copper ($\lambda$=398 W/(m·K)), aluminum ($\lambda$=237 W/(m·K)), iron ($\lambda$=84 W/(m·K)), phosphor bronze ($\lambda$=60 W/(m·K)), or stainless steel ($\lambda$=17 W/(m·K)) is used.

As the housing 60, a material having high thermal conductivity $\lambda$, for example, a material same as the material of the heat transfer member 30 may be used. However, as the material of the heat transfer member 30, it is desirable to use a material having the thermal conductivity $\lambda$ higher than the thermal conductivity $\lambda$ of the housing 60. For example, it is particularly desirable that the housing 60 is formed of stainless steel and the heat transfer member 30 is formed of copper.

Note that, as a joining member for joining the heat transfer member 30 and the image pickup device 20, it is desirable to use an adhesive made of resin having high thermal conductivity. The thermal conductivity of the joining member is desirably 1 W/(m·K) or more and particularly desirably 15 W/(m·K) or more.

As the joining member, low-melting point metal such as solder may be used. By joining the heat transfer member 30 and the image pickup device 20 using metal having higher thermal conductivity compared with the resin, it is possible to more efficiently transfer heat. When a conductive material such as a metal material is used for the joining, it goes without saying that it is necessary to prevent contact with an electric connection section.

A method of manufacturing the image pickup apparatus 1 is explained.

First, a plurality of image pickup devices 20 including the light receiving sections 21 are formed on a silicon substrate using a publicly-known semiconductor process. After a glass wafer having substantially the same size as the silicon substrate is bonded on a formation surface of the light receiving sections 21 as a protection material, cutting is performed from a rear surface side of the silicon substrate. After thickness of the silicon substrate is reduced by the cutting, a through-hole is formed by etching or the like from the rear surface side. An insulating film is formed on a sidewall of the formed through-hole. An inside of the through-hole is made conductive by conductive paste, a plating method, a sputtering method, or the like, whereby the through-wire 22 is formed. Thereafter, the silicon substrate bonded with the glass wafer is singulated by cutoff, whereby the image pickup device 20 bonded with the cover glass 10 is manufactured.

In the wiring board 40, the electrode pads 42 and 45 and the wire 43 are manufactured by sticking together and etching a copper foil and a polyimide or the like, which is a base material, and using the plating method. The electronic component 44 is mounted on the wiring board 40.

The heat transfer member 30 is manufactured by, for example, pressing and etching a copper plate. To facilitate bending of the bending section 30V, local heat treatment or the like may be applied to only the bending section 30V by laser radiation or the like. Then, the bending section 30V is bent and plastically deformed to set the length between the end portion of the fixed section 30Y1 and the end portion of the fixed section 30Y2 to W3.

The length W3 only has to be larger than the inner dimension W1 of the housing 60. However, when easiness of insertion into the housing and a balance with intensity of an urging force are taken into account, it is desirable that the length W3 is 110% or more and 200% or less of W1.

Note that a shape memory alloy such as a titanium-nickel alloy may be used as the material of the heat transfer member 30. That is, after the bending section 30V of the heat transfer member 30, which memorizes a state in which the bending section 30V is deformed and the fixed section 30Y is largely open, is bent and housed in the housing, by heating the heat transfer member 30 to a predetermined temperature, the fixed section 30Y can be pressed against the inner surface of the housing 60 by an urging force.

The joining section 30X of the heat transfer member 30 is joined to the second principal plane 20SB of the image pickup device 20 by a joining member. At this point, the joining section 30X is joined such that the external connection terminal 23 of the image pickup device 20 is located on the inside of the through-hole 30H of the heat transfer member 30.

Subsequently, the electrode pad 42 of the wiring board 40, to which the cable 50 is connected, and the external connection terminal 23 of the image pickup device 20 are joined. A periphery of the joining section 30X may be sealed by resin such that the resin is injected into the through-hole 30H.

An image pickup unit, in which the cover glass 10, the image pickup device 20, the heat transfer member 30, the wiring board 40, and the signal cable 50 are integrated, is inserted into the inside of the housing 60. A plan view shape and an inner dimension of the housing 60 are substantially the same as and slightly larger than a plan view shape and an outer dimension of the image pickup device 20. For example, the inner dimension W1 in a longitudinal direction of the housing 60 shown in FIG. 3 is almost the same as the outer dimension W2 in the longitudinal direction of the image pickup device 20.

The resin 62 is filled in the inside of the housing 60, whereby the image pickup apparatus 1 is completed.

As explained above, the heat transfer member 30 is in contact with the housing 60 made of metal while being pressed against the housing 60. Note that, an elastic body is used as a material of the heat transfer member 30. The heat transfer member 30 is pressed against the inner surface of the housing 60 to be deformed by adjusting thickness, dimensions, a shape, and the like of the heat transfer member 30. The heat transfer member 30 can be set in surface contact with the housing 60. By setting the heat transfer member 30 in surface contact with the housing 60, it is possible to more efficiently transfer heat generated in the image pickup device 20 to the housing 60.

The image pickup apparatus 1 can efficiently radiate the heat generated by the image pickup device 20. The image pickup apparatus 1 is small in diameter because the heat transfer member 30 and the wiring board 40 are housed in a housing having an inner dimension same as an outer dimension of the image pickup device 20.

<Modification of the First Embodiment>

As shown in FIG. 4, in the heat transfer member 30 of the image pickup apparatus 1, the bending sections 30V1 and 30V2 and the fixed sections 30Y1 and 30Y2 respectively extend from two opposed sides of the joining section 30X.

Figure 5:
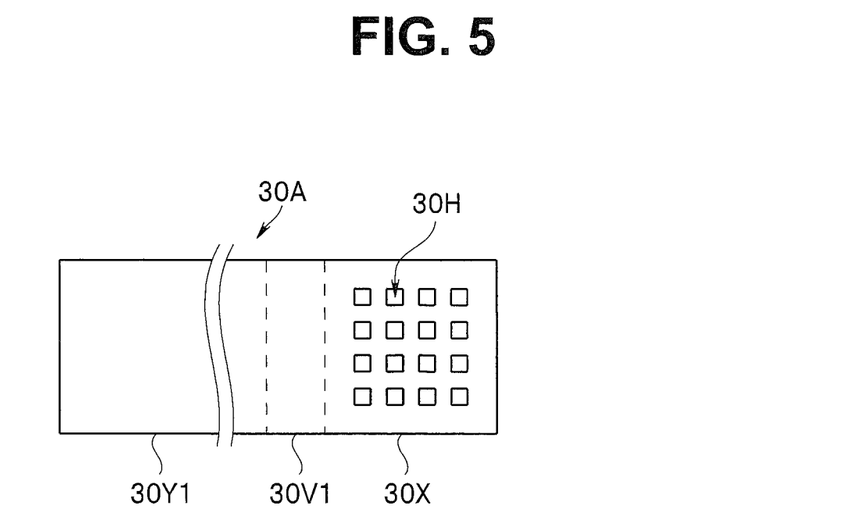
FIG. 5 is a plan view of a heat transfer member of an image pickup apparatus in a modification 1 of the first embodiment.

On the other hand, in a heat transfer member 30A in a modification 1 shown in FIG. 5, the bending section 30V1 and the fixed section 30Y1 extend from one side of the joining section 30X.

Figure 6:
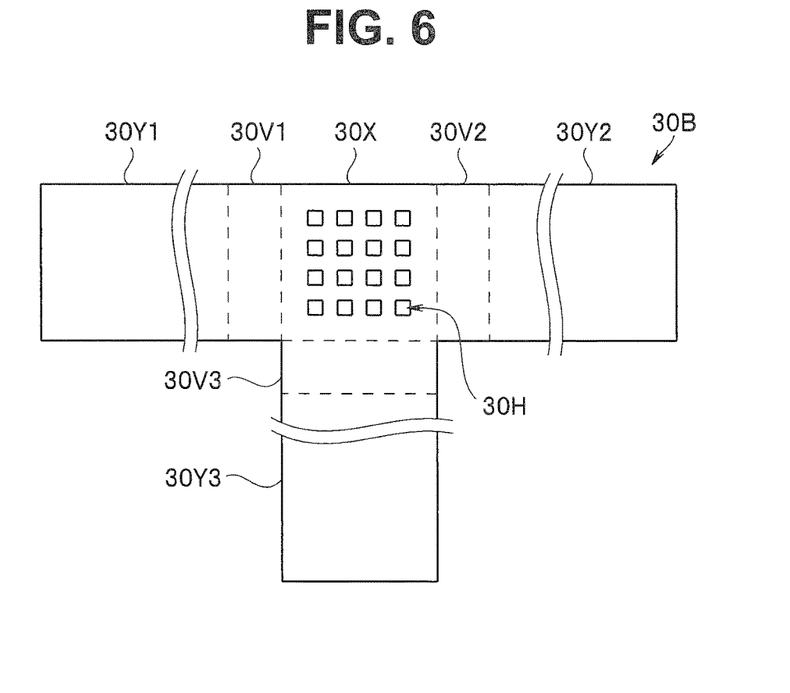
FIG. 6 is a plan view of a heat transfer member of an image pickup apparatus in a modification 2 of the first embodiment.

In a heat transfer member 30B in a modification 2 shown in FIG. 6, bending sections 30V1, 30V2, and 30V3 and fixed sections 30Y1, 30Y2, and 30Y3 extend from three sides of the joining section 30X.

Figure 7:
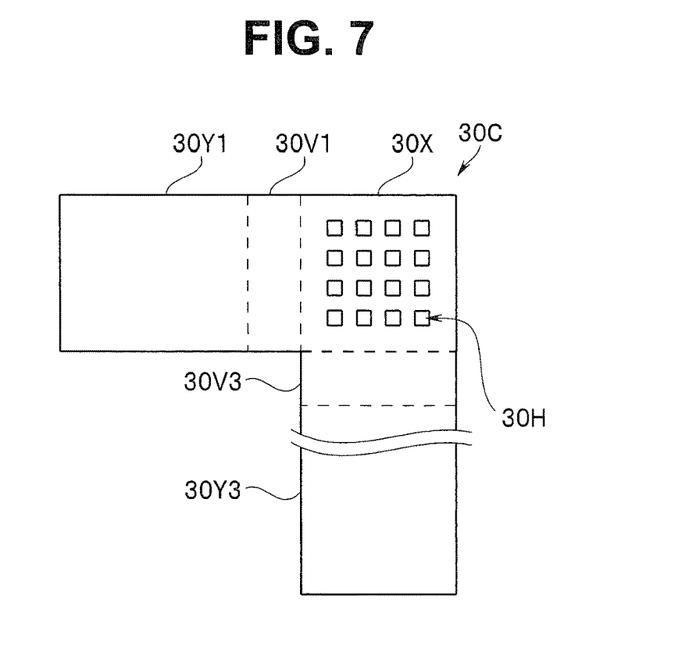
FIG. 7 is a plan view of a heat transfer member of an image pickup apparatus in a modification 3 of the first embodiment.

In a heat transfer member 30C in a modification 3 shown in FIG. 7, the bending sections 30V1 and 30V3 and the fixed sections 30Y1 and 30Y3 extend from orthogonal two sides of the joining section 30X.

Image pickup apparatuses in the modifications 1 to 3 including the heat transfer members 30A, 30B, and 30C have effects same as the effects of the image pickup apparatus 1 in the first embodiment. Note that a shape of the heat transfer member is selected according to disposition of the wiring board 40, the electronic component 44, and the signal cable 50 disposed on the inside of the housing 60, a heat value of the image pickup device, that is, a heat quantity that should be radiated, and the like.

Second Embodiment

An image pickup apparatus 1D in a second embodiment is explained. Since the image pickup apparatus 1D is similar to the image pickup apparatus 1 and the like, the same components are denoted by the same reference numerals and signs and explanation of the components is omitted.

Figure 8:
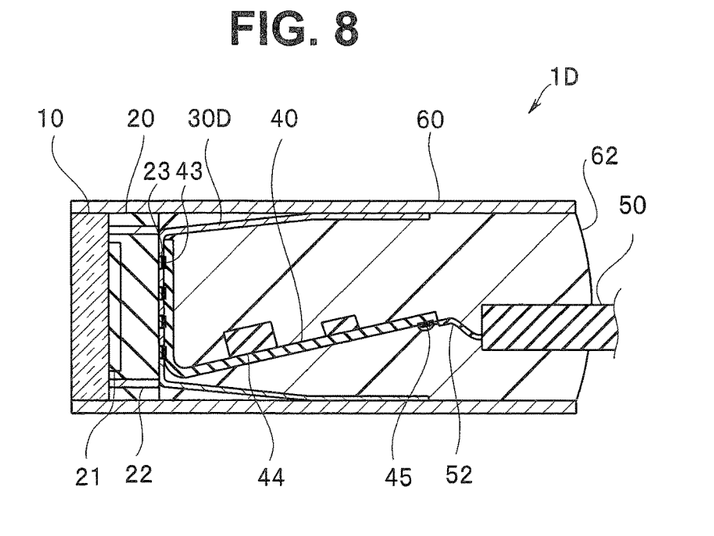
FIG. 8 is a sectional view of an image pickup apparatus in a second embodiment.
Figure 9:
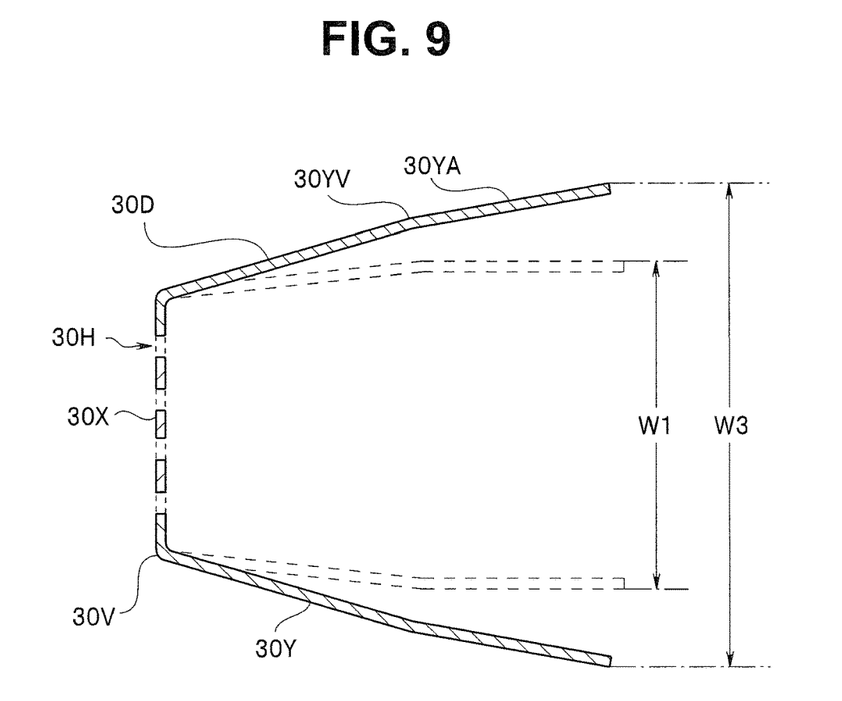
FIG. 9 is a sectional view of a heat transfer member of an image pickup apparatus in the second embodiment.

As shown in FIG. 8 and FIG. 9, a heat transfer member 30D of the image pickup apparatus 1D includes a bending section 30YV in the fixed section 30Y. The bending section 30YV is plastically deformed in advance such that, when the heat transfer member 30D is housed in the housing 60, a distal end portion 30YA of the fixed section 30Y is parallel to the inner surface of the housing 60. Therefore, an entire surface of the distal end portion 30YA is in surface contact with the inner surface of the housing 60.

The image pickup apparatus 1D has effects same as the effects of the image pickup apparatus 1. Further, since a contact area of the heat transfer member 30D and the housing 60 is large, it is possible to more efficiently radiate the heat generated by the image pickup device 20.

Third Embodiment

An image pickup apparatus 1E in a third embodiment is explained. Since the image pickup apparatus 1E is similar to the image pickup apparatus 1 and the like, the same components are denoted by the same reference numerals and signs and explanation of the components is omitted.

Figure 10:
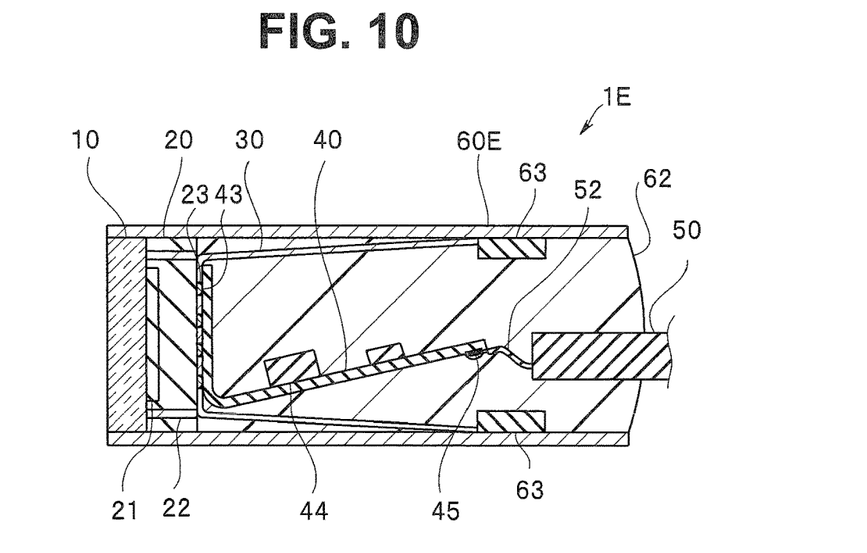
FIG. 10 is a sectional view of an image pickup apparatus in a third embodiment.

As shown in FIG. 10, on an inner surface of a housing 60E of the image pickup apparatus 1E, a positioning section 63 that defines a position in a longitudinal direction of the fixed section 30Y on an inside of the housing 60E, that is, a position in the longitudinal direction of an image pickup unit is disposed.

As explained above, an image pickup unit, in which the cover glass 10, the image pickup device 20, the heat transfer member 30, the wiring board 40, and the signal cable 50 are integrated, is inserted into the inside of the housing 60E from a distal end side. At this point, a disposition position in the longitudinal direction of the image pickup unit is defined by the positioning section 63.

The positioning section 63 may be formed by disposing a separate member or may be formed by machining a part of the housing 60E. A part of the fixed section 30Y may be machined to provide a convex section to be locked to or engaged with the positioning section 63.

The image pickup apparatus 1E has effects same as the effects of the image pickup apparatus 1 and the like. Further, it is possible to easily secure accuracy of a disposition position of the image pickup unit, for example, the image pickup device 20.

<Modification of the Third Embodiment>

Figure 11:
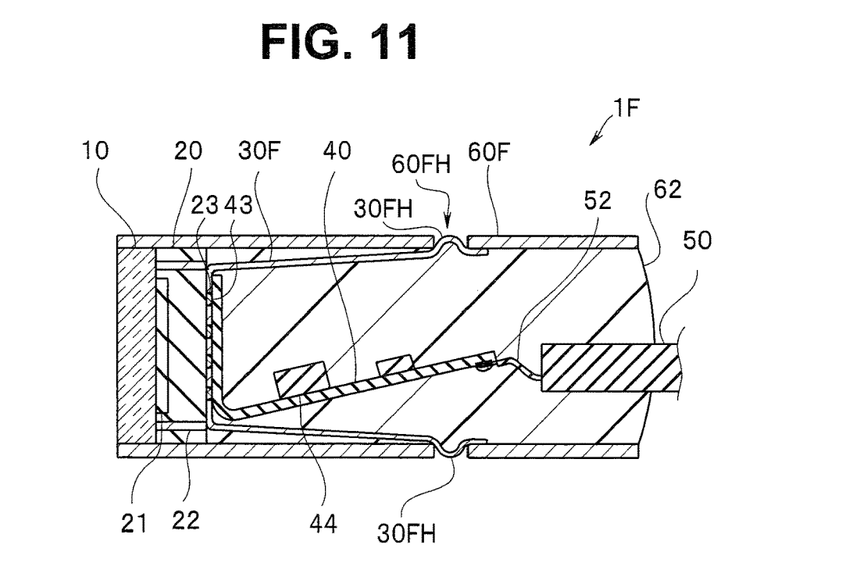
FIG. 11 is a sectional view of an image pickup apparatus in a modification of the third embodiment.

In an image pickup apparatus 1F of a modification shown in FIG. 11, an elongated hole 60FH is formed on a contact surface of a heat transfer member 30F of a housing 60F. A part of the fixed section 30Y of the heat transfer member 30F is machined into a convex section 30FH to fit with a hole 60FH. That is, the hole 60FH of the housing 60F is a positioning section having a function of a positioning member that defines a position of a fixed section.

Note that, after the heat transfer member 30F and the housing 60F are fit, a material having high thermal conductivity such as high thermal conduction resin, solder, or Ag paste may be injected into the hole 60FH to fix and seal a part where the housing 60F and the heat transfer member 30F are in contact.

The image pickup apparatus 1F in the modification has the effects of the image pickup apparatus 1E. Further, since the hole 60FH of the housing 60F and the convex section 30FH of the fixed section 30Y are fit, a contact area is large. When a contact portion of the housing 60F and the convex section 30FH of the heat transfer member 30F is sealed by a high thermal conductivity material, heat is more efficiently transferred.

Fourth Embodiment

An image pickup apparatus 1G in a fourth embodiment is explained. Since the image pickup apparatus 1G is similar to the image pickup apparatus 1 and the like, the same components are denoted by the same reference numerals and signs and explanation of the components is omitted.

Figure 12:
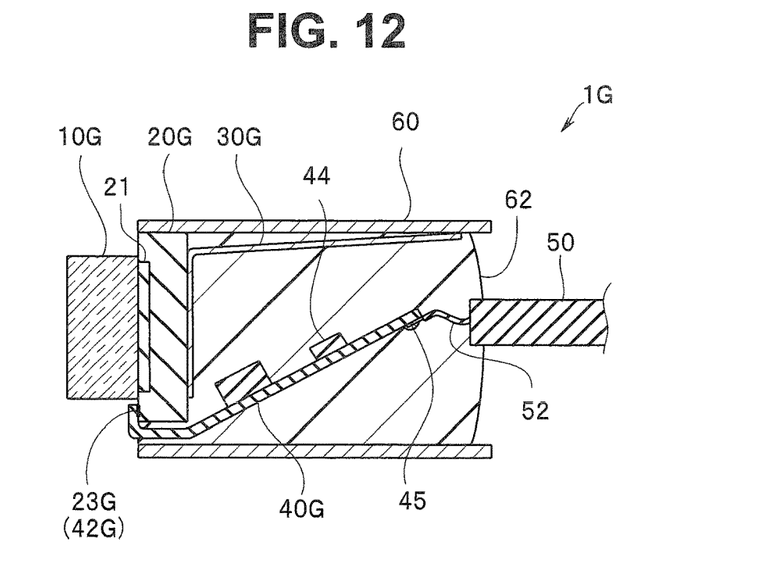
FIG. 12 is a sectional view of an image pickup apparatus in a fourth embodiment.

As shown in FIG. 12, in an image pickup device 20G of the image pickup apparatus 1G, an external connection terminal 23G is disposed on the first principal plane 20SA. One end portion of a wiring board 40G is connected to the external connection terminal 23G on the first principal plane 20SA of the image pickup device 20G. The other end portion is disposed on a rear end side via a bending section.

The image pickup apparatus 1G has the effects of the image pickup apparatus 1 and the like. Further, it is easy to manufacture the image pickup device 20G without a through-wire. The through-hole 30H is absent in a joining section 30XG of a heat transfer member 30G. Therefore, it is easy to manufacture the heat transfer member 30G. Further, since a contact area of the image pickup device 20G and the heat transfer member 30G is large, it is possible to efficiently radiate heat generated by the image pickup device 20G.

Fifth Embodiment

Figure 13:
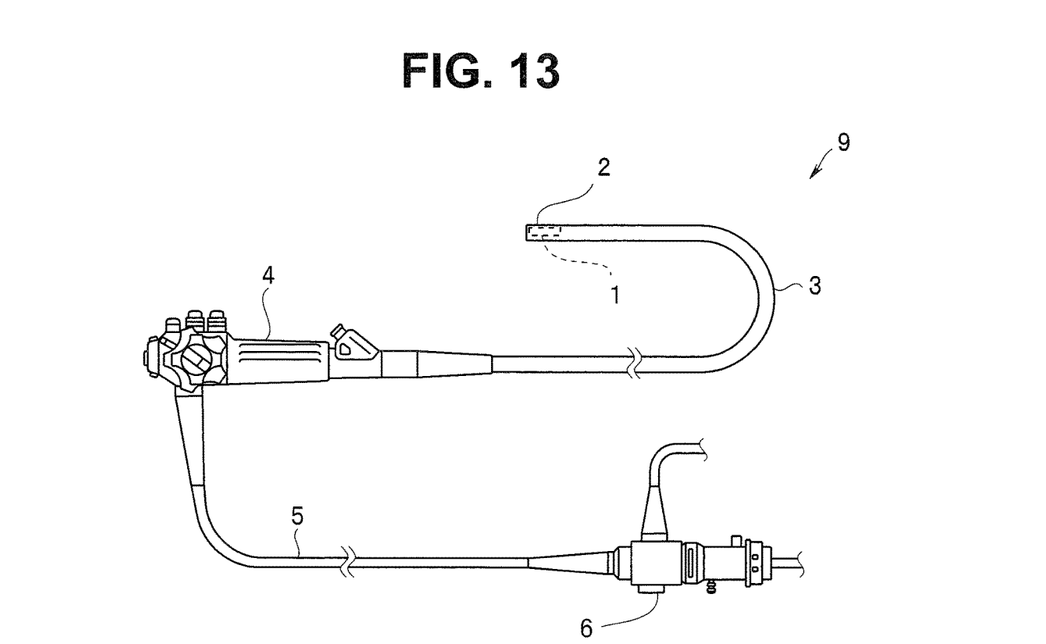
FIG. 13 is an exterior view of an endoscope in a fifth embodiment.

An endoscope 9 in a fifth embodiment is explained. As shown in FIG. 13, the endoscope 9 is an electronic endoscope including the image pickup apparatus 1 in the first embodiment at a distal end portion 2 of an insertion section 3.

The endoscope 9 includes an operation section 4 disposed on a proximal end side of the insertion section 3 and a universal cord 5 extending from the operation section 4. In the operation section 4, various switches and the like, which a surgeon operates while grasping the operation section 4, are disposed. The cable 50 of the image pickup apparatus 1 is inserted through the insertion section 3 and the universal cord 5 and connected to a main body section (not shown in the figure), which performs image processing and the like, via a connector 6 disposed at a proximal end portion of the universal cord 5.

Since the image pickup apparatus 1 is small in diameter and very small is size, the endoscope 9 including the image pickup apparatus 1 at the distal end portion is less invasive. In the endoscope 9, it is unlikely that the image pickup apparatus 1 is deteriorated by an excessive temperature rise and image quality is deteriorated by thermal noise.

Note that it goes without saying that endoscopes including the image pickup apparatuses 1A to 1G in the embodiments and the modifications instead of the image pickup apparatus 1 in the first embodiment also have effects same as the effects of the endoscope 9 in the present embodiment.

The present invention is not limited to the embodiments, the modifications, and the like. Various changes, alterations, and the like can be made in a range in which the gist of the present invention is not changed.

What is claimed is:
1. An image pickup apparatus comprising:
    an image pickup sensor including a first principal plane and a second principal plane, in which a light receiving section is formed on the first principal plane;

a wiring board including a device electrode pad connected to an external connection terminal of the image pickup sensor and a wire, one end of the wire being connected to the device electrode pad;

a heat transfer member formed of a material having a thermal conductivity equal to or higher than 15 W/(m·K), the heat transfer member comprising:
   a joining section joined to the second principal plane of the image pickup sensor,
   a bending section extending from the joining section, and
   a fixed section extending from the bending section in an extending direction from the first principal plane towards the second principal plane;

a housing formed of metal for containing the heat transfer member on an inside of the housing, an inner surface of the housing being in contact with a portion of the fixed section of the heat transfer member, wherein the wiring board is entirely disposed within a volume defined by an area of the image pickup sensor projected in the extending direction, and the fixed section is biased by the bending section to contact with a portion of the inner surface of the housing such that heat generated by the image pickup sensor is transferred to the housing by the heat transfer member.

2. The image pickup apparatus according to claim 1, wherein at least the bending section of the heat transfer member is made of an elastic material and exerts a biasing force to the fixed section.

3. The image pickup apparatus according to claim 2, wherein the bending section comprises a plurality of bending sections and the fixed section comprises a plurality of fixed sections.

4. The image pickup apparatus according to claim 2, wherein the portion of the fixed section comprises a flat surface that is in surface contact with the inner surface of the housing.

5. The image pickup apparatus according to claim 1, wherein the housing comprises a positioning section that defines a position of the fixed section on the inside of the housing.

6. The image pickup apparatus according to claim 5, wherein the fixed section comprises a convex section that is in contact with the housing.

7. The image pickup apparatus according to claim 1, wherein
   the image pickup sensor includes a through-wire that extending through the first principal plane and the second principal plane, and the external connection terminal is disposed on the second principal plane, and
   a through-hole of the heat transfer member is arranged in a position opposed to the external connection terminal of the image pickup sensor.

8. The image pickup apparatus according to claim 1, wherein the external connection terminal is disposed on the first principal plane of the image pickup sensor.

9. An endoscope comprising the image pickup apparatus according to claim 1.

10. The endoscope according to claim 9, wherein at least the bending section of the heat transfer member is made of an elastic material and exerts a biasing force to the fixed section.

11. The endoscope according to claim 10, wherein the bending section comprises a plurality of bending sections and the fixed section comprises a plurality of fixed sections.

12. The endoscope according to claim 10, wherein the portion of the fixed section comprises a flat surface that is in surface contact with the inner surface of the housing.

13. The endoscope according to claim 9, wherein the housing comprises a positioning section that defines a position of the fixed section on the inside of the housing.

14. The endoscope according to claim 13, wherein the fixed section comprises a convex section that is in contact with the housing.

15. The endoscope according to claim 9, wherein
   the image pickup sensor includes a through-wire that extending through the first principal plane and the second principal plane, and the external connection terminal is disposed on the second principal plane, and
   a through-hole of the heat transfer member is arranged in a position opposed to the external connection terminal of the image pickup sensor.

\* \* \* \* \*